(12) United States Patent
Lo et al.

(10) Patent No.: US 8,575,223 B2
(45) Date of Patent: *Nov. 5, 2013

(54) CREAM FOR APPLYING ON A BODY

(71) Applicant: D & Y Laboratories, Holden, MO (US)

(72) Inventors: Shui Yin Lo, Pasadena, CA (US); David L. Gann, Holden, MO (US); Martine Gann, Holden, MO (US)

(73) Assignee: D&Y Laboratories, Holden, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/751,796

(22) Filed: Jan. 28, 2013

(65) Prior Publication Data

US 2013/0142884 A1 Jun. 6, 2013

Related U.S. Application Data

(63) Continuation-in-part of application No. 12/592,877, filed on Dec. 3, 2009, now Pat. No. 8,383,688.

(60) Provisional application No. 61/611,981, filed on Mar. 16, 2012.

(51) Int. Cl.
*A61K 47/00* (2006.01)
*C01B 5/00* (2006.01)

(52) U.S. Cl.
USPC .......... 514/769; 423/580.1; 977/832

(58) Field of Classification Search
USPC .......... 514/769; 423/580.1; 977/832
See application file for complete search history.

(56) References Cited

U.S. PATENT DOCUMENTS 8,193,251 B2 * 6/2012 Lo et al. .......... 514/769
8,383,688 B2 * 2/2013 Lo et al. .......... 514/769

* cited by examiner

*Primary Examiner* — Raymond Henley, III
(74) *Attorney, Agent, or Firm* — Henry M. Feiereisen, LLC

(57) ABSTRACT

A cream has at least two components, one of the components includes stable water clusters, and the cream is applied on a body to produce local surface effects, local deep effects, and non-local effects in the body.

15 Claims, No Drawings

CREAM FOR APPLYING ON A BODY

CROSS-REFERENCE TO RELATED APPLICATIONS

This patent application is a continuation-in-part of patent application Ser. No. 12/592,873 filed on Dec. 3, 2009 now U.S. Pat. No. 8,193,251 and of patent application Ser. No. 12/592,877 filed on Dec. 3, 2009, now U.S. Pat. No. 8,383,688 whose subject matter is incorporated here by reference thereto, and this patent application also claims its priority from patent application Ser. No. 12/592,873 and Ser. No. 12/599,877 under 35 USC 119(a)-(e).

This patent application also claims its priority from provisional patent application Ser. No. 61/611,981 filed on Mar. 18, 2012, whose subject matter is incorporated here by reference thereto, and this patent application also claims its priority from provisional patent application Ser. No. 61/611,981 under 35 USC 119(a)-(e).

BACKGROUND OF THE INVENTION

The present invention relates generally to creams, and in particular to cream for applying on a body of humans and animals.

Creams of these types are known in the art in great varieties. The creams can be applied on a body for purely cosmetic purposes, they also can be applied on the body for health enhancing purposes, and sometimes they can be applied on the body for achieving both above mentioned results. It is believed that the existing creams can be further improved.

SUMMARY OF THE INVENTION

Accordingly, it is an object of the present invention to provide a new cream for applying on a body, which is a further improvement of existing creams.

It is also an object of the present invention to provide a method of health enhancement with the use of the new cream.

In keeping with these objects and with others which will become apparent hereinafter, one feature of the present invention resides, briefly stated, in a cream for applying on a body, which has at least one first component including stable water clusters.

When the cream in accordance with the present invention is applied on a body, in particular on a skin, stable water clusters which have nanometric sizes, easily penetrate the skin and cause health enhancing results which will be explained in detail hereinbelow.

In accordance with a further feature of the present invention, in the inventive cream the stable water clusters of its at least one first component are formed as double-helix water clusters.

It is still a further feature of the present invention that the at least one first component includes a mixture of pure water and water with the above-mentioned stable water clusters.

The cream in accordance with the present invention further includes at least one second component, which is mixed with the above mentioned first component of the cream.

In accordance with a further feature of the present invention, the second component of the inventive cream can be an organic component.

The second component of the inventive cream can include a plant ingredient, or an animal ingredient, or a nutrient supplement ingredient, or various combinations of two or three above mentioned ingredients.

As for the second ingredient of the cream in accordance with the present invention. In the second component of the cream the plant ingredient can include oils, the animal ingredient can include beeswax, the nutrient supplement ingredient can include vitamins.

The present invention also deals with a method of health enhancement, which includes applying on a body a cream which has at least one first component including stable water clusters.

In accordance with the present invention, the cream with the first component including the stable water clusters is applied on a skin of the body of a human or an animal.

In accordance with the inventive method, the cream made in accordance with the present invention can be applied on an area of the skin, which has health problem, in order to alleviate these skin problems.

The cream in accordance with the present invention can be also applied on the skin so that it penetrates the skin and enhances health of internal organs of the body, such as muscles, tissues, bones.

The cream in accordance with the present invention can be also applied on acupoints and dispersed throughout the body so as to enhance health of internal organs and systems in correspondence with respective acupoints.

The novel features of the present invention are set forth in particular in the appended claims.

The invention itself, however, both as to its construction and its method of operation, is disclosed in detail in the following description of the preferred embodiments.

DESCRIPTION OF THE PREFERRED EMBODIMENTS

With the present invention, a new cream for applying on a body of a human or an animal is proposed. The cream in accordance with the present invention has at least one first component including stable water clusters.

The stable water clusters are produced as disclosed in our patent application Ser. No. 12/592,873 filed on Dec. 3, 2009, which is now U.S. Pat. No. 8,193,251 issued on Jun. 5, 2012. The stable water clusters are those stable water clusters which are disclosed and described in detail in our patent application Ser. No. 12/592,877 filed on Dec. 3, 2009, whose description is incorporated herein by reference thereto.

The cream in accordance with the present invention is used for applying on a body, in particular on a skin, and the stable water clusters which are contained in it and have nanometric sizes, easily penetrate the skin and produce health enhancing results.

In the inventive cream the stable water clusters which are contained in its at least one first component can be double-helix water clusters. It is to be understood however that the stable water clusters of other configurations can be also utilized in the first component of the cream.

The at least one first component includes a mixture of pure water and water with the above-mentioned stable water clusters. The pure water is preferably a very pure water which has 16 mega ohm or better resistance with low total organic carbon less than 100 ppm, and it mixed with the water which contains the stable water clusters. The amount of the water with the stable water clusters in the cream in accordance with the present invention is preferably 40% or less by weight from total weight of the cream.

The cream in accordance with the present invention further includes at least one second component, which is mixed with the above mentioned first component of the cream. The second component of the inventive cream preferably can be an organic component.

The second component of the inventive cream can include a plant ingredient, an animal ingredient, a nutrient supplement ingredient. It can also various combinations of two or three of the above mentioned ingredients, which are mixed with each other.

When the second component of the cream is a plant ingredient it can include for example oils. When the second component of the cream is an animal ingredient it can include for example beeswax. When the second component of the cream is a nutrient supplement ingredient it can include for example vitamins. The oil for example can be coconut oil, sweet almond oil, lecithin, etc, and various combinations thereof. The vitamin for example can be vitamin E, another vitamin, and various combinations thereof.

The cream in accordance with the present invention, in addition to the above mentioned first and second components, can also include small amounts of scent, or fragrance, or preservatives, which are known per se in the art.

In order to make the cream in accordance with the present invention, first water with stable water clusters is made in a manner described in detail in our above mentioned patent applications and patent, and then mixed with very pure water, so as to produce the first component of the cream. Then the second component of the cream is produced by mixing its ingredients. The water mixture of the ingredients of the first component is warmed up, the mixture of the ingredients of the second component is heated up and added to the first component, the thusly produced mixture is stirred and heated together until the inventive cream is formed. It is then cooled down to room temperature and is ready to either be stored, or packed into individual containers for consumption.

It should be mentioned that the temperature of the mixtures of the first and second components should be greater than the freezing temperature of water (0° C.) and lower than the boiling temperature of water (100° C.), so that its water component remains in liquid state.

The cream in accordance with the present invention is used for health enhancing purposes of a human body or an animal body. In accordance with one embodiment the cream is used to achieve an effect which is local and on a surface. In this case the inventive cream is applied substantially on an area of the skin which has skin problems. In this case the cream may be used for baby rash on buttocks, for a mosquito bite on a face, for itches on the skin, for burns of the skin, etc. The cream for a respective one of the above mentioned health problems can have a slightly different composition. In the case this local and surface application of the cream, it can be also used for cosmetic purposes to produce a smooth and better looking skin.

The cream in accordance with the present invention further can be used to produce local deep effects in the body. In this case the cream is rubbed to reach a corresponding depth to penetrate through the skin and into desired organs of the body. In this embodiment the cream produces health enhancing effects for example on such organs as muscles, tissues, bones. In this case it can be also efficiently utilized for sport use.

In accordance with a further embodiment of the invention, the inventive cream can be also used for non-local effects. In this case it can be applied on acupoints and rubbed in there, so that it is dispersed throughout the body via meridian system. For example, is the inventive cream is rubbed on the acupoint ST4 near the mouth, it will have an effect on stomach and digestive system.

One example of the cream in accordance with the present invention is presented in the Table hereinbelow.

TABLE 1

| Components | Quantity |
|---|---|
| Bees Wax | 2.5 ounces |
| Coconut Oil | 2 ounces |
| Sweet Almond Oil | 6 ounces |
| Ultra Pure Water With | |
| 1.5 fl. oz. of Water With | |
| Stable Water Clusters | 6.5 ounces |
| Lecithin | 2,400 mg |
| Vitamin E Oil | 400 IU. |

The present invention is not limited to the details shown since various modifications and structural changes are possible without departing from the spirit of the invention.

What is desired to be protected by Letters Patent is set forth in particular in the appended claims.

The invention claimed is:

1. A cream for applying on a body, comprising at least one first component including stable water clusters.

2. A cream as defined in claim 1, wherein said at least one first component includes the stable water clusters formed as double-helix water clusters.

3. A cream as defined in claim 1, wherein said at least one first component includes pure water and water which contains the stable water clusters.

4. A cream as defined in claim 1, further comprising at least one second component mixed with said at least one first component.

5. A cream as defined in claim 4, wherein said at least one second component is an organic component.

6. A cream as defined in claim 4, wherein said at least one second component includes an ingredient selected from the group consisting of a plant ingredient, an animal ingredient, a nutrient supplement ingredient, and combination thereof.

7. A cream as defined in claim 6, wherein said plant ingredient of said at least one second component includes oil.

8. A cream as defined in claim 6, wherein said animal ingredient of said at least one second component includes beeswax.

9. A cream as defined in claim 6, wherein said nutrient supplement ingredient of said at least one second component includes vitamin.

10. A cream as defined in claim 3, wherein said water with stable water clusters has a weight of substantially not more than 40% of a weight of the cream.

11. A method of health enhancing, comprising the step of applying on a body a cream which has at least one component including stable water clusters.

12. A method as defined in claim 1, wherein said applying includes applying the cream which has at least one component including stable water clusters, on a skin of the body.

13. A method as defined in claim 12, wherein said applying the cream which has at least one component including stable water clusters, on the skin of the body includes applying the cream on an area of the skin, which has a skin problem.

14. A method as defined in claim 12, wherein said applying the cream which has at least one component including stable water clusters, on the skin of the body includes applying the cream so that it penetrates into the body to enhance health of interior organs selected from the group consisting of muscles, tissues, and bones.

15. A method as defined in claim 12, wherein said applying the cream which has at least one component including stable water clusters, on the skin includes applying the cream on acupoints and thereby dispersing it throughout the body to enhance health of internal organs and systems.

\* \* \* \* \*

UNITED STATES PATENT AND TRADEMARK OFFICE
CERTIFICATE OF CORRECTION

PATENT NO. : 8,575,223 B2  
APPLICATION NO. : 13/751796  
DATED : November 5, 2013  
INVENTOR(S) : Shui Yin Lo et al.

Page 1 of 1

It is certified that error appears in the above-identified patent and that said Letters Patent is hereby corrected as shown below:

Title page, item [73] Assignee: should read as follows: D & Y Laboratories, Holden, MO (US)

Signed and Sealed this  
Seventeenth Day of December, 2013

Margaret A. Focarino  
*Commissioner for Patents of the United States Patent and Trademark Office*